United States Patent [19]

Niwa et al.

[11] Patent Number: 4,699,982
[45] Date of Patent: Oct. 13, 1987

[54] PERINONE COMPOUND

[75] Inventors: Toshio Niwa, Kanagawa; Kiyoshi Himeno; Junji Yoshihara, both of Fukuoka, all of Japan

[73] Assignee: Mitsubishi Chemical Industries Limited, Tokyo, Japan

[21] Appl. No.: 772,518

[22] Filed: Sep. 4, 1985

[30] Foreign Application Priority Data

Sep. 4, 1984 [JP] Japan .................................. 59-184828

[51] Int. Cl.$^4$ ..................... C07D 487/16; C09B 57/12
[52] U.S. Cl. ........................................ 544/245; 8/648
[58] Field of Search ......................................... 544/245

[56] References Cited

U.S. PATENT DOCUMENTS 4,268,671 5/1981 Imahori et al. ..................... 544/245

FOREIGN PATENT DOCUMENTS 0010936 4/1973 Japan .
0039823 11/1973 Japan .

OTHER PUBLICATIONS

Arient et al., Chemical Abstracts, vol. 71, 9624v (1969).
Okada et al., Chemical Abstracts, vol. 80, 146970q (1974).
Okada et al., Chemical Abstracts, vol. 81, 65224t (1974).
Okada et al., Chemical Abstracts, vol. 81, 107367z (1974).

Primary Examiner—Donald G. Daus
Assistant Examiner—Diana G. Rivers
Attorney, Agent, or Firm—Sughrue, Mion, Zinn, Macpeak, and Seas

[57] ABSTRACT

A perinone compound represented by the formula

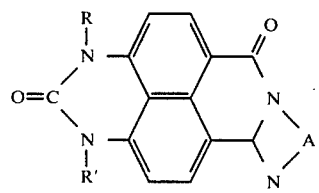

wherein R represents arylene; R and R', which may be the same or different, each represents alkoxyalkyl, hydroxyalkyl, N,N-dialkylaminoalkyl, cycloalkyl or aralkyl; and X represents oxygen or sulfur. The perinone compound fluoresces a yellowish green to orange color and is useful as a fluorescent dye or dyestuff.

6 Claims, No Drawings

PERINONE COMPOUND

FIELD OF THE INVENTION

This invention relates to a novel perinone compound. More particularly, it relates to a perinone compound which has a fluorescent color of from a yellowish green to orange color and can be utilized as a fluorescent dye or dyestuff.

BACKGROUND OF THE INVENTION

In recent years, field of utilizing dyes or dyestuffs having intense fluorescent property has been rapidly broadened. For example, fluorescent dyes or dye-stuffs have shown more variety in application, such as not only in dyeing or printing various synthetic fiber materials, dope coloring of various synthetic resins, melt spinning-dyeing, as fluorescent pigments in fluorescent dyes or inks, etc. but also in colored laser beams, solar batteries as a convergent system, display devices, and the like.

The present inventors have previously found that the following compounds A and B are fluorescent dyes having excellent fastness to light:

Compound A:

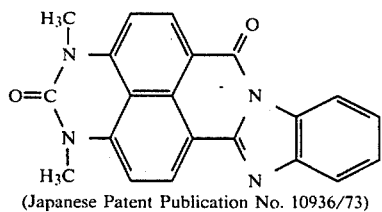

(Japanese Patent Publication No. 10936/73)

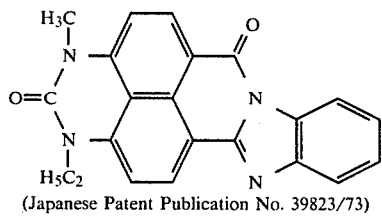

(Japanese Patent Publication No. 39823/73)

However, these compounds involve a problem in practical use from the standpoint of affinity for organic substrates. In some detail, when they are used as disperse dyes for dyeing polyester cloth, they were of low practical use due to their poor build-up property and temperature dependence. Further, when they are used as fluorescent pigments in combination with resin components, such as toluenesulfonamide, formaldehyde, melamine, etc., the compatibility with these resin components is poor, resulting in low fluorescent intensity and fastness to light when being spread on a paper substrate, etc.

SUMMARY OF THE INVENTION

Accordingly, an object of this invention is to provide a highly practical perinone compound having good affinity for various organic substrates.

More particularly, an object of this invention is to provide a perinone compound having satisfactory build-up property and temperature dependence when used as a dye and having excellent fluorescent property and fastness to light when used as a fluorescent pigment.

The perinone compound according to the present invention is a compound represented by the formula (I)

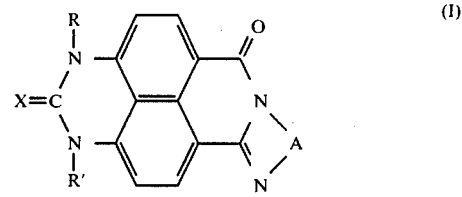

wherein A represents substituted or unsubstituted arylene; R and R', which may be the same or different, each represents alkoxyalkyl, hydroxyalkyl, N,N-dialkylaminoalkyl, cycloalkyl or aralkyl; and X represents oxygen or sulfur.

DETAILED DESCRIPTION OF THE INVENTION

In the above-described formula (I), examples of arylene represented by A include o-phenylene, naphthylene, etc. which may be substituted with, for example, alkyl, alkoxy, alkoxyalkyl, nitro, halogen, etc. Of those, o-phenylene is preferred.

Alkoxyalkyl represented by R and R' contains from 1 to 10, and preferably from 1 to 4, carbon atoms in its alkoxy moiety and contains from 1 to 10, and preferably from 1 to 4, carbon atoms in its alkyl moiety. Examples thereof include methoxyethyl, ethoxyethyl, butoxyethyl, methoxypropyl, ethoxypropyl, n-propoxypropyl, isopropoxypropyl, butoxypropyl, 2-ethylhexyloxypropyl, etc.

Hydroxyalkyl represented by R and R' contains from 1 to 4 carbon atoms and examples thereof include hydroxyethyl, hydroxypropyl, hydroxybutyl, etc.

Example of N,N-dialkylaminoalkyl represented by R and R' include N,N-dimethylaminoethyl, N,N-dimethylaminopropyl, N,N-diethylaminoethyl, N,N-diethylaminopropyl, etc.

Examples of cycloalkyl represented by R and R' include cyclohexyl, etc.

Examples of aralkhyl represented by R and R' include benzyl, phenethyl, etc.

In the present invention, the compounds of the formula (I) wherenin R and R' each represents alkoxyalkyl are particularly preferred as dyes.

In the formula (I), X represents oxygen or sulfur, and oxygen is preferred.

The perinone compound represented by the formula (I) according to the present invention can be prepared by the following processes A and B:

Process A comprises reacting a compound represented by the formula (II)

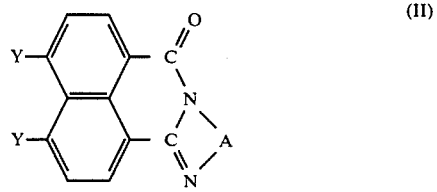

wherein A is the same as defined above; and Y represents halogen, with a compound represented by the formula (III)

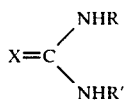

(III)

wherein R, R' and X are the same as defined above, in the presence of an inert solvent, such as nitrobenzene, nitrotoluene, etc., by heating to thereby form a perimidone ring or a thioperimidone ring.

Process B comprises reacting a compound represented by the formula (IV)

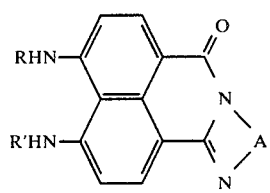

(IV)

wherein A, R and R' are the same as defined above, with a carbonylating agent or thiocarbonylating agent in the presence of an organic solvent, such as chlorobenzene, etc., to thereby form a perimidone ring or a thioperimidone ring.

The perinone compounds (I) according to the present invention exhibit excellent properties as fluorescent dyes or dyestuffs.

Fibers which can be dyed with the compounds of the present invention include polyester fibers composed of polyethylene terephthalate, a polycondensate between terephthalic acid and 1,4-bis(hydroxymethyl)cyclohexane, or the like; and blended fabric goods or blended textile goods e.g., cloth, textile, fabric, etc.) composed of the above-described polyester fibers and natural fibers, such as cotton, silk, wool, etc.

In carrying out dyeing using the compounds of present invention, the compound of the formula (I) is dispersed in an aqueous dispersing medium using a dispersing agent in conventional manner to prepare a dye bath or a printing paste, and dip dyeing or printing is then conducted using the same.

In the case of dip dyeing, polyester fibers, or blended fabric goods or blended textile goods thereof can be dyed to have excellent fastness by applying conventional dyeing methods, such as high temperature dyeing, carrier dyeing, thermosol dyeing, and the like. In some cases, further improved results can be attained by adding an acidic substance to a dye bath.

Polyester fibers or mixed yarns thereof dyed with the compounds of the present invention by the above-described methods show an extremely clear hue with brilliance by the synergistic effect of the fluorescent color (yellowish green to orange) of the dye with the reflective color of the dyed articles. Further, the dyed articles have superior fastness to light. Moreover, the compounds according to the present invention have extremely excellent build-up property and temperature dependence during dyeing.

The compounds according to the present invention can also be applied to coloring of various organic polymeric materials including fibers. The coloring can be carried out at any optional stage of from the production of the material to be colored through the processing thereof. For example, the coloring can be effected by the so-called dope-dyeing method in which the fluorescent dyestuff of the formula (I) is added to a spinning dope before spinning in the manufacture of fibers. Further, in the case of coloring thin films or plates, good results can also be obtained by a method in which the fluorescent dyestuff is incorporated into a molding material before or during the molding process. Examples of the synthetic resin molded articles by these coloring methods include polystyrene resins, acrylic resins, polycarbonate resins, ABS resins, polyethylene resins, etc. Those coloring methods can also be applied to polyethylene, polyvinyl chloride, etc.

The compounds of the present invention can further be employed as dyestuffs for fluorescent coating films. Coating films having excellent fluorescent property and fastness to light can be produced by mixing the compound of the present invention with resin components, such as toluenesulfonamide, formamide, melamine, etc., diluting the mixture with an acrylic varnish, etc., and coating the resulting varnish on a substrate, such as paper, metal plates, etc.

Furthermore, the compounds of the present invention can effectively be used as dyestuffs for fluorescent synthetic resin plates or films of a convergent system for solar batteries because of their high fastness to light, and as dyestuffs for fluorescence-activated display elements.

In addition, the compounds of the present invention are suitable as laser dyes in wavelength region of from 450 to 560 nm for dye laser apparatuses which are given pulse by $N_2$ laser.

The present invention will now be illustrated in greater detail by reference to the following examples and comparative examples, but it should be understood that the present invention is not limited thereto.

EXAMPLE 1

0.5 g of a perinone compound of the formula

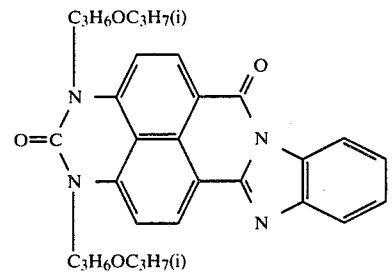

was dispersed in 3 liters of water containing 1.0 g of a naphthalenesulfonic acid-formaldehyde condensate and 2.0 g of a higher alcohol sulfuric acid ester to prepare a dye bath.

100 g of polyester cloth was dipped in the dye bath and dyed at 130° C. for 60 minutes, followed by soaping, washing with water, and drying, to obtain a polyester cloth dyed in fluorescent greenish yellow and having excellent fastness to light, fastness to sublimation and wet color fastness.

The above-described perinone compound was determined for temperature dependence and build-up property in accordance with the methods described below. The results obtained are shown in Table 1.

Temperature Dependence

Dip dyeing was carried out under the dyeing conditions of 120° C.×60 minutes and 130° C.×60 minutes according to the same process as described in Example 1, and the ratio of the amount of the dye of the dyed cloth (120° C./130° C.) was determined. The amount of the dye was measured by solvent extraction of the dyed cloth with dimethylformamide.

Build-Up Property

Dip dyeing was carried out in the same manner as described in Example 1 but using 1.0 g (1 owf) or 0.5 g (0.5 owf) of the dye cake, and the degree of exhaustion of the dye (the amount of dye exhausted/the amount of dye used ×100) was determined.

The perinone compound used in this example was prepared as follows.

20 g of a perinone compound of the formula

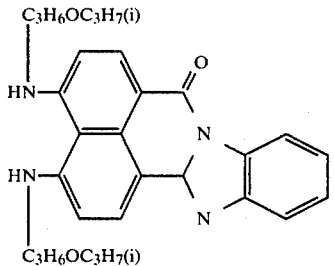

was reacted with 45.6 g of N,N-diethylaminoaniline and 30 g of ethyl chloroformate in chlorobenzene at 130° C. for 1.5 hours. After cooling, the reaction mixture was filtered, and the solid was washed successively with methanol and water to obtain 13.6 g of yellow crystals. The maximum absorption wavelength ($\lambda_{max}$) (in acetone) of the dye was 450 nm.

EXAMPLE 2

0.5 g of a dye of the formula

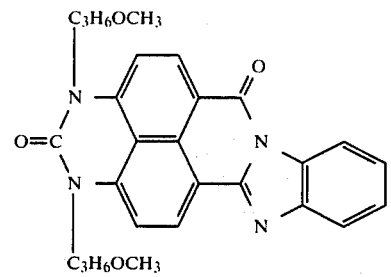

was mixed with 0.5 g of a naphthalenesulfonic acid-formaldehyde condensate, and the mixture was finely pulverized in a paint shaker to obtain a powdery dye. The resulting powdery dye was thoroughly blended with a stock paste having the following composition to prepare a color paste.

| Stock Paste Composition: | |
|---|---|
| Carboxymethyl cellulose-based paste | 30.0 g |
| Tartaric acid | 0.2 g |
| Aromatic carrier ("SUNFLOWREN SN", a trade name, manufactured by Nikka Chemistry Co., Ltd.) | 0.3 g |
| Water | 68.5 g |
| Total: | 99.0 g |

The resulting color paste was printed on a polyester cloth, intermediately dried at 100° C., held in superheated steam at 170° C. for 7 minutes to develop a color, followed by soaping, washing with water and drying, to obtain a cloth dyed in fluorescent yellow and having excellent fastness to light, fastness to sublimation and wet color fastness. The $\alpha_{max}$ (in acetone) of the dye was 450 nm.

The above-described perinone compound was determined for temperature dependence and build-up property in the same manner as in Example 1. The results obtained are shown in Table 1.

COMPARATIVE EXAMPLES 1 AND 2

Conventional dyes having the similar structure to the compounds of the present invention as shown in Table 1 were tested for temperature dependence and build-up property in the same manner as in Example 1. The results obtained are shown in Table 1 below.

TABLE 1

| Example No. | Structural Formula of Dye Used | Temperature Dependence (120° C./130° C.) (%) | Build-up Property (1% dye concentration/ 0.5% dye concentration) (%) |
|---|---|---|---|
| Example 1 | (structure shown) | 95 | 95 |

TABLE 1-continued

| Example No. | Structural Formula of Dye Used | Temperature Dependence (120° C./130° C.) (%) | Build-up Property (1% dye concentration/ 0.5% dye concentration) (%) |
|---|---|---|---|
| Example 2 | [structure with C₃H₆OCH₃ groups on N, naphthalimide-benzimidazole] | 95 | 92 |
| Comparative Example 1* | [structure with CH₃ groups on N, naphthalimide-benzimidazole] | 60 | 55 |
| Comparative Example 2* | [structure with CH₃ and C₂H₅ groups on N, naphthalimide-benzimidazole] | 60 | 60 |

Note:
*dye disclosed in Japanese Patent Publication No. 10936/73.
**dye disclosed in Japanese Patent Publication No. 39823/73.

EXAMPLE 3

Polyester cloth was dyed in the same manner as described in Example 1 but using compounds shown in Table 2 below (Compound Nos. 1 to 35). The $\lambda_{max}$ of the compounds, color tone of the dyed cloth, temperature dependence and build-up property of the dyes were determined in the same manner as in Example 1.

The results obtained are shown in Table 2.

TABLE 2

[General structure: naphthalimide core with X=C, N-R, N-R', and fused N=A ring]

| Compound No. | X | R and R' | A | $\lambda_{max}$ (acetone) (mm) | Color Tone | Temperature Dependence (120° C./130° C.) (%) | Build-Up Property (1% dye concentration 0.5% dye concentration) (%) |
|---|---|---|---|---|---|---|---|
| 1 | O | H₃COC₂H₄— | [benzene ring] | 452 | fluorescent yellow | 96 | 90 |
| 2 | O | H₅C₂OC₂H₄— | [benzene ring] | 452 | fluorescent yellow | 95 | 92 |

TABLE 2-continued

[Structure: naphthalene core with R-N and R'-N groups connected via X=C on one side, and a triazole ring (N-N with A substituent) with a C=O group on the other side]

| Compound No. | X | R and R' | A | $\lambda_{max}$ (acetone) (mm) | Color Tone | Temperature Dependence (120° C./130° C.) (%) | Build-Up Property (1% dye concentration 0.5% dye concentration) (%) |
|---|---|---|---|---|---|---|---|
| 3 | O | $H_5C_2OC_3H_6-$ | benzene | 450 | fluorescent yellow | 95 | 95 |
| 4 | O | $(n)H_7C_3OC_3H_6-$ | benzene | 450 | fluorescent yellow | 95 | 95 |
| 5 | O | $(i)H_9C_4OC_3H_6-$ | benzene | 450 | fluorescent yellow | 92 | 92 |
| 6 | O | $(n)H_9C_4OC_3H_6-$ | benzene | 450 | fluorescent yellow | 92 | 90 |
| 7 | O | $H_9C_4-CH-OC_3H_6-$ <br> $\phantom{xxx}\|$ <br> $\phantom{xxx}C_2H_5$ | benzene | 450 | fluorescent yellow | 90 | 90 |
| 8 | O | $H_3COC_3H_6-$ | benzene-$CH_3$ | 456 | fluorescent yellow | 95 | 92 |
| 9 | O | $(i)H_7C_3OC_3H_6-$ | benzene-$CH_3$ | 456 | fluorescent yellow | 95 | 95 |
| 10 | O | $(i)H_7C_3OC_3H_6-$ | benzene-$OCH_3$ | 463 | fluorescent yellow | 92 | 92 |
| 11 | O | $(i)H_7C_3OC_3H_6-$ | benzene-$Cl$ | 448 | fluorescent yellow | 90 | 92 |
| 12 | O | $(i)H_7C_3OC_3H_6-$ | naphthalene | 460 | fluorescent yellow | 90 | 90 |
| 13 | O | $(i)H_7C_3OC_3H_6-$ | naphthalene | 480 | fluorescent orange | 90 | 90 |

TABLE 2-continued

[Structure: naphthalene core with R-N=C(X)-N-R' group on one side and N-A (with N=) triazole-like ring on other side, plus C=O group]

| Compound No. | X | R and R' | A | $\lambda_{max}$ (acetone) (mm) | Color Tone | Temperature Dependence (120° C./130° C.) (%) | Build-Up Property (1% dye concentration 0.5% dye concentration) (%) |
|---|---|---|---|---|---|---|---|
| 14 | S | HOC$_2$H$_4$— | phenyl | 480 | fluorescent orange | 90 | 90 |
| 15 | S | HOC$_2$H$_4$— | 4-methylphenyl (CH$_3$) | 486 | fluorescent orange | 90 | 90 |
| 16 | O | HOC$_2$H$_4$— | 4-methylphenyl (CH$_3$) | 458 | fluorescent yellow | 92 | 92 |
| 17 | O | (H$_3$C)$_2$NC$_2$H$_4$— | phenyl | 452 | fluorescent yellow | 90 | 90 |
| 18 | O | cyclohexyl-H | phenyl | 450 | fluorescent yellow | 90 | 85 |
| 19 | O | C$_6$H$_5$CH$_2$— | phenyl | 450 | fluorescent yellow | 90 | 85 |
| 20 | O | C$_6$H$_5$C$_2$H$_4$— | phenyl | 451 | fluorescent yellow | 85 | 85 |
| 21 | S | H$_3$COC$_3$H$_6$— | phenyl | 480 | fluorescent orange | 90 | 92 |
| 22 | S | (i)H$_7$C$_3$OC$_3$H$_6$— | phenyl | 480 | fluorescent orange | 92 | 92 |
| 23 | S | H$_5$C$_2$OC$_2$H$_4$— | phenyl | 482 | fluorescent orange | 92 | 90 |
| 24 | S | cyclohexyl-H | phenyl | 482 | fluorescent orange | 90 | 90 |

TABLE 2-continued

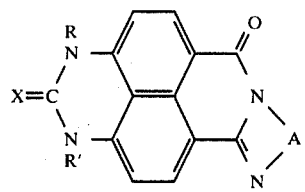

| Compound No. | X | R and R' | A | $\lambda_{max}$ (acetone) (mm) | Color Tone | Temperature Dependence (120° C./ 130° C.) (%) | Build-Up Property (1% dye concentration 0.5% dye concentration) (%) |
|---|---|---|---|---|---|---|---|
| 25 | S | benzyl (C₆H₅CH₂—) | o-tolyl | 482 | fluorescent orange | 90 | 90 |
| 26 | S | benzyl (C₆H₅CH₂—) | naphthyl (1,8) | 528 | fluorescent red | 85 | 85 |
| 27 | S | (i)H₇C₃OC₃H₆— | naphthyl (1,8) | 526 | fluorescent red | 90 | 85 |
| 28 | S | H₃COC₃H₆— | naphthyl (1,8) | 526 | fluorescent red | 90 | 90 |
| 29 | O | H₃COC₃H₆— | naphthyl (1,8) | 480 | fluorescent yellow | 90 | 90 |
| 30 | O | H₅C₂OC₃H₆— | naphthyl (1,8) | 480 | fluorescent yellow | 90 | 90 |
| 31 | O | H₃COC₃H₆—/(i)H₇C₃OC₃H₆— | o-phenylene | 450 | fluorescent yellow | 98 | 98 |
| 32 | O | H₃COC₃H₆—/(i)H₇C₃OC₃H₆— | 4-methyl-o-phenylene | 456 | fluorescent yellow | 98 | 98 |
| 33 | O | H₃COC₃H₆—/H₅C₂OC₃H₆— | o-phenylene | 450 | fluorescent yellow | 96 | 96 |
| 34 | O | H₃COC₃H₆—/H₅C₂OC₃H₆— | 4-methoxy-o-phenylene | 463 | fluorescent yellow | 96 | 95 |

TABLE 2-continued

[Structure: perinone compound with R-N and R'-N groups on naphthalene, X=C bridge, and N-A substituent]

| Compound No. | X | R and R' | A | λ_max (acetone) (mm) | Color Tone | Temperature Dependence (120° C./130° C.) (%) | Build-Up Property (1% dye concentration 0.5% dye concentration) (%) |
|---|---|---|---|---|---|---|---|
| 35 | O | $H_3COC_3H_6-/H_5C_2OC_3H_6-$ | [2,4-dimethylphenyl structure with CH_3] | 456 | fluorescent yellow | 95 | 95 |

EXAMPLE 4

With 1,000 parts by weight of polystyrene pellets were blended 0.2 part by weight of the same perinone dyestuff as used in Example 1, and the blend was kneaded at 200° to 240° C. and then injection-molded to produce a colored plate having a thickness of 2 mm. During these operations, thermal decomposition of the dyestuff, discoloration or a like phenomenon was not at all observed.

The dye exhibited satisfactory dispersibility in and compatibility with the polystyrene. The resulting polystyrene plate was uniformly colored and had an extremely clear fluorescent greenish yellow color. When the colored plate was exposed to light for 100 hours using a fadeometer, neither reduction in fluorescence nor change in color was observed.

EXAMPLES 5 TO 7 AND COMPARATIVE EXAMPLES 3 TO 4

18 g of a o- and p-mixed toluenesulfoneamideformamide resin was heat-melted at 70° C., and 20 g of melamine was added thereto and 130° C. Ten minutes later, 14.3 g of p-formaldehyde was added thereto. After the temperature was further elevated to 170° C., 0.5 g of a perinone compound shown in Table 3 below was added thereto, followed by stirring for 15 minutes.

Then, the mixture was cooled and the thus solidified fluorescent yellow pigment was finely pulverized. The powdering pigment was thoroughly mixed with 1.5 times the amount of a cold-setting acrylic varnish, and the resulting varnish was spread on art paper using a 8 mil applicator. The resulting coated paper had an extremely clear fluorescent yellow color.

The color developability of the pigment was evaluated by determining the reflectance at the maximum reflectance wavelength ($\lambda_{max}$) by means of a Macbeth photometer (MS-2020).

Further, the coated paper was exposed to light for 300 hours using a fadeometer, and the fastness to light was evaluated by a gray scale.

The results obtained are shown in Table 3 below.

TABLE 3

| Example No. | Structural Formula of Perinone Compound | Color Developability (reflectance %/reflectance $\lambda_{max}$ nm) | Fastness to light (grade) |
|---|---|---|---|
| Example 5 | $C_3H_6OC_3H_7(i)$ substituted perinone with phenyl group; both N bear $C_3H_6OC_3H_7(i)$ | 190/540 | 4–5 |
| Example 6 | $C_3H_6OCH_3$ substituted perinone with phenyl group; both N bear $C_3H_6OCH_3$ | 180/540 | 4–5 |

TABLE 3-continued

| Example No. | Structural Formula of Perinone Compound | Color Developability (reflectance %/ reflectance λ$_{max}$ nm) | Fastness to light (grade) |
| --- | --- | --- | --- |
| Example 7 | (C$_2$H$_4$OH substituted structure) | 190/540 | 4 |
| Comparative Example 3 | (CH$_3$ substituted structure) | 120/540 | 3 |
| Comparative Example 4 | (CH$_3$/C$_2$H$_5$ substituted structure) | 120/540 | 3 |

While the invention has been described in detail and with reference to specific embodiments thereof, it will be apparent to one skilled in the art that various changes and modifications can be made therein without departing from the spirit and scope thereof.

What is claimed is:

1. A perinone compound represented by the formula

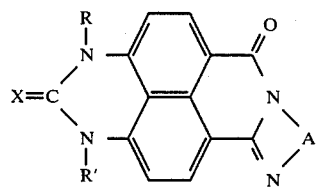

wherein A represents unsubstituted arylene; R and R', which may be the same or different, each represents alkoxyalkyl or hydroxyalkyl; and X represents oxygen or sulfur.

2. A perinone compound as in claim 1, wherein A is o-phenylene.

3. A perinone compound as in claim 1, wherein R and R' each is alkoxyalkyl.

4. A perinone compound as in claim 3, wherein R and R' each is alkoxyalkyl containing from 1 to 4 carbon atoms in its alkoxy moiety and from 1 to 4 carbon atoms in its alkyl moiety.

5. A perinone compound as in claim 1, wherein X is oxygen.

6. A perinone compound as in claim 1, wherein A is naphthylene.

* * * * *